United States Patent
DuBourdieu et al.

(10) Patent No.: US 12,076,374 B1
(45) Date of Patent: Sep. 3, 2024

(54) ANTI-MICROBIAL AND ANTI-INFLAMMATORY COMPOSITIONS AND METHODS FOR TREATING ENTERIC DISEASES IN ANIMALS

(71) Applicant: Vets Plus, Inc., Menomonie, WI (US)

(72) Inventors: Daniel J. DuBourdieu, Limerick, ME (US); Rajiv Lall, Menomonie, WI (US); Ajay Srivastava, Menomonie, WI (US); Jamil Talukder, Menomonie, WI (US)

(73) Assignee: Vets Plus, Inc., Menomonie, WI (US)

( * ) Notice: Subject to any disclaimer, the term of this patent is extended or adjusted under 35 U.S.C. 154(b) by 0 days.

(21) Appl. No.: 16/733,714

(22) Filed: Jan. 3, 2020

Related U.S. Application Data (60) Provisional application No. 62/788,199, filed on Jan. 4, 2019.

(51) Int. Cl.
| | |
|---|---|
| *A61P 1/00* | (2006.01) |
| *A61K 9/00* | (2006.01) |
| *A61K 31/12* | (2006.01) |
| *A61K 31/722* | (2006.01) |
| *A61K 36/28* | (2006.01) |
| *A61K 36/48* | (2006.01) |
| *A61K 36/53* | (2006.01) |
| *A61K 36/54* | (2006.01) |
| *A61K 36/61* | (2006.01) |
| *A61K 36/67* | (2006.01) |
| *A61K 36/71* | (2006.01) |
| *A61K 36/88* | (2006.01) |
| *A61K 36/9068* | (2006.01) |
| *A61K 38/40* | (2006.01) |
| *A61K 45/06* | (2006.01) |

(52) U.S. Cl.
CPC ............ *A61K 38/40* (2013.01); *A61K 9/0056* (2013.01); *A61K 31/12* (2013.01); *A61K 31/722* (2013.01); *A61K 36/28* (2013.01); *A61K 36/48* (2013.01); *A61K 36/53* (2013.01); *A61K 36/54* (2013.01); *A61K 36/61* (2013.01); *A61K 36/67* (2013.01); *A61K 36/71* (2013.01); *A61K 36/88* (2013.01); *A61K 36/9068* (2013.01); *A61K 45/06* (2013.01); *A61P 1/00* (2018.01)

(58) Field of Classification Search
None
See application file for complete search history.

(56) References Cited

U.S. PATENT DOCUMENTS

| | | | |
|---|---|---|---|
| 10,213,490 B2 | 2/2019 | Bromley et al. | |
| 10,905,748 B2 | 2/2021 | Talukder et al. | |
| 2011/0200591 A1* | 8/2011 | Bisgaard-Frantzen | ...................... A23C 9/206 530/387.3 |
| 2017/0182133 A1 | 6/2017 | Bromley et al. | |
| 2019/0314460 A1 | 10/2019 | Talukder et al. | |

FOREIGN PATENT DOCUMENTS

| | | | |
|---|---|---|---|
| CN | 106721243 | * | 5/2017 |
| WO | WO 2014/071207 | * | 5/2014 |

OTHER PUBLICATIONS

Kidibule et al., Microbial cell factories, 17, 47, 2018.*
Ajay Srivastava, Rajiv Lall, Jamil Talukder, Dan DuBourdieu, Ramesh C Gupta. Iron Transport Tocopheryl Polyethylene Glycol Succinate in Animal Health and Diseases. Molecules. Nov. 25, 2019;24(23):4289.
Aller Choice. Derm health. For support with dermatological sensitivities and overall skin health. Soft Chews for Dogs. Product Detail Sheet: Mar. 18, 2019. Clinics Choice, Acworth, GA 30101. Sold: Mar. 27, 2019.
Derm Choice—gel. Derm health. For support of overall dermotological health. Topical gel for dogs. Product Detail Sheet: Mar. 18, 2019. Clinics Choice, Acworth, GA 30101. Sold: Mar. 27, 2019.
Derm Choice—shampoo and conditioner. Derm health. For support of overall skin and coat health. Topical shampoo for Dogs. Product Detail Sheet: Mar. 18, 2019. Clinics Choice, Acworth, GA 30101. Sold: Mar. 27, 2019.
Flex Choice. Joint health. For support in overall mobility and healthy joint function. Powder for Cats. Product Detail Sheet: Mar. 18, 2019. Clinics Choice, Acworth, GA 30101. Sold: Mar. 27, 2019.
Flex Choice. Joint Health. For support in overall mobility and healthy joint function. Soft Chews for Dogs. Product Detail Sheet: Mar. 18, 2019. Clinics Choice, Acworth, GA 30101. Sold: Mar. 27, 2019.
Flora Choice—daily. Gut support. For support of daily and long term gut health. Powder for Cats & Dogs. Product Detail Sheet: Mar. 18, 2019. Clinics Choice, Acworth, GA 30101. Sold: Mar. 27, 2019.
Liver Choice. Hepatic support. For support of healthy hepatic function, and overall liver health. Soft Chews for Dogs. Product Detail Sheet: Mar. 18, 2019. Clinics Choice, Acworth, GA 30101. Sold: Mar. 27, 2019.
LysiPluc Choice. Immune support. For support of a healthy immune system and overall feline wellness. Powder for Cats. Product Detail Sheet: Mar. 18, 2019. Clinics Choice, Acworth, GA 30101. Sold: Mar. 27, 2019.

(Continued)

*Primary Examiner* — Michael V Meller
(74) *Attorney, Agent, or Firm* — Daniel A. Blasiole; DeWitt LLP (57) ABSTRACT

The present invention is a composition intended for consumption by animals containing antimicrobials and anti-inflammatory agents, which may include ovotransferrin, chitosan, and *Curcumin*. The composition may be provided as powder that is mixed into feeds, may be incorporated into pellets, or may be delivered through water, among other methods of dosage. The invention is intended as a health supplement for increased gain and improved general health in production animals affected by enteric diseases such as coccidiosis and as a general health supplement in humans and companion animals facing enteric diseases to maintain the gut microbiome.

19 Claims, 3 Drawing Sheets

(56) References Cited

OTHER PUBLICATIONS

Ora Choice—pro. Dental health. For support of overall dental health. Dental Sticks for Dogs. Product Detail Sheet: Mar. 18, 2019. Clinics Choice, Acworth, GA 30101. Sold: Mar. 27, 2019.

Oti Choice. Derm health. For support of overall ear health. Topical for Dogs. Product Detail Sheet: Mar. 18, 2019. Clinics Choice, Acworth, GA 30101. Sold: Mar. 27, 2019.

Pancre Choice. Pancreatic support. For support in healthy pancreatic function vital to maintain overall health. Powder for Dogs. Product Detail Sheet: Mar. 18, 2019. Clinics Choice, Acworth, GA 30101. Sold: Mar. 27, 2019.

Pill Choice. Pill sleeves. Made with real peanut butter. Fits most tablets and capsules. Soft Chews for Dogs. Product Detail Sheet: Mar. 18, 2019. Clinics Choice, Acworth, GA 30101. Sold: Mar. 27, 2019.

Recov Choice. Energy support. Energy support. Helps maintain electrolyte balance. Manages the nutrient uptake. Gel for Dogs. Product Detail Sheet: Mar. 18, 2019. Clinics Choice, Acworth, GA 30101. Sold: Mar. 27, 2019.

Travel Choice. Gut support. For support of a normal, healthy digestive system. Gel for Dogs. Product Detail Sheet: Mar. 18, 2019. Clinics Choice, Acworth, GA 30101. Sold: Mar. 27, 2019.

Arabkhazaeli F., Modrisanei M, Nabian S., Mansoori B. and Madani A. Evaluating the Resistance of *Eimeria* Spp. Field Isolates to Anticoccidial Drugs Using Three Different Indices. *Iran J Parasitol.* Apr.-Jun. 2013; 8(2): 234-241.

Epstein, J.; Sanderson, I. R .; MacDonald, T. T. Curcumin as a therapeutic agent: the evidence from in vitro, animal and human studies. *British Journal of Nutrition*, 2010, 103, 11, pp. 1545-1557. FDA 2017; https://www.fda.gov/animalveterinary/developmentapprovalprocess/ucm449019.htm.

Giansanti F., Loris Leboffe, Francesco Angelucci and Giovanni Antonini. The Nutraceutical Properties of Ovotransferrin and Its Potential Utilization as a Functional Food. *Nutrients* 2015, 7, 9105-9115.

Kantere, M., Athanasiou L.V., Chatzopoulos D.C., Spyrou V., Valiakos G., Kontos V. and Billinis C. Enteric Pathogens of Dogs and Cats with Public Health Implications. *American Journal of Animal and Veterinary Sciences* 2014, 9(2): 84-94.

Lam G, Apostolopoulos V, Zulli A, Nurgali K. NADPH oxidases and inflammatory bowel disease. *urr Med Chem.* 2015; 22 (17) 2100-9.

Lambert LA, Perri H, Halbrooks PJ, Mason AB. Evolution of the transferrin family: conservation of residues associated with iron and anion binding. *Comp Biochem Physiol B Biochem Mol Biol.* Oct. 2005; 142(2):129-41.

Petri WA, Miller M, Binder Hj, Levine MM, Dillingham R., and Guerrant RL. Enteric infections, diarrhea, and their impact on function and development. *The Journal of Clinical Investigation*, 2008; 118 (4) 1277-1290.

Pircalabioru et al. Defensive mutualism rescues NADPH oxidase inactivation in gut infection. *Cell Host & Microbe* 19, 651-663 May 11, 2016.

Ragab M. El-Sabagh, Mabrouk, Attia Abd Eldaim. Effects of Spirulina Platensis Algae on Growth Performance, Antioxidative Status and Blood Metabolites in Fattening Lambs. *Journal of Agricultural Science*, 2014, vol. 6, No. 3 p. 92-98.

Raafat D., Kristine von Bargen, Albert Haas, and Hans-Georg Sahlahboub & Mohamed Abdel-Daim. Insights into the Mode of Action of Chitosan as an Antibacterial Compound. *Applied and Environmental Microbiology*, Jun. 2008, p. 3764-3773 vol. 74.

Talukder MJR and Harada E. Bovine lactoferrin protects lipopolysaccharide-induced diarrhea modulating nitric oxide and prostaglandin E2 in mice. *Can. J. Physiol. Pharmacol.* 2007, 85(2): 200-8.

Talukder JR, Ashley Griffin, Antara Jaima, Brittney Boyd, and Jaleesa Wright, Lactoferrin ameliorates prostaglandin E2-mediated inhibition of Na-glucose cotransport in enterocytes. *Can J. Physiol. Pharmacol,* 2014; 92: 9-20.

Theil EC. The ferritin family of iron storage proteins. *Adv Enzymol Relat Areas Mol Biol.* 1990; 63:421-49.

\* cited by examiner

ANTI-MICROBIAL AND ANTI-INFLAMMATORY COMPOSITIONS AND METHODS FOR TREATING ENTERIC DISEASES IN ANIMALS

FIELD OF THE INVENTION

The present invention is directed to methods for improving gut health in animals such as companion animals or humans, and directed to feed supplements and alternatives to antibiotics as growth promoters for production animals

BACKGROUND

Enteric Diseases

Health issues caused by enteric pathogens are a prominent public health challenge in the USA. Enteric diseases account for multi-million-dollar annual economic losses to the food animal industry due to reduced weight gain, mortality of young animals, and treatment costs. For humans that consume infected food the cost can be incalculable. Companion animals also suffer enteric diseases, some of which can be passed on to humans. The incidence of diseases caused by enteric pathogens, and food- and water-borne pathogens is high, and some diseases are increasing, despite many concerted efforts to control various enteric pathogens in production animals.

Production animals are faced with numerous health challenges before they reach maturity and full potential. Many of these health challenges start in the gut of the animal and typically are the result of enteric diseases. These enteric diseases can occur at any point in the life of the animal and during transitional times in mammals such as at weaning time. Treatment and prevention of these enteric diseases typically utilize drugs such as antibiotics. However, the indiscriminate use of antibiotics for growth production has now been banned in many countries and alternatives to these antibiotics are required to accomplish safe and effective production. Enteric diseases in animals range across all production species commonly used, including chickens, pigs, sheep, and cattle. In many instances these enteric diseases result in diarrhea.

The use of antibiotics in food production has resulted in tremendous increases in growth promotion in food animals. Studies have shown that administering low doses (subtherapeutic levels) of antibiotics in livestock feed improves growth rate, reduces mortality and morbidity, and improves reproductive performance. The mechanism by which antibiotic growth promoters work is not clear. One theory is that antibiotic growth promoters reduce normal intestinal flora (which compete with the host for nutrients) and harmful gut bacteria (which may reduce performance by causing subclinical disease). The effect on growth may be due to a combination of both fewer normal intestinal flora and fewer harmful bacteria. Other possibilities include metabolic effects, disease control effects, and nutritional effects.

However, another important aspect of why antibiotics may improve growth is that with reduced pathogenic bacteria present, less inflammation of the gut might be occurring. The realization that chronic, low-grade tissue inflammation is an important factor in the pathogenesis of a variety of chronic diseases has been an important advancement in the scientific understanding of the mechanism by which the disease is caused. Inflammation is a natural protective process in which the white blood cells release various chemical mediators. One of the more important chemical mediators of inflammation are a group of compounds called prostaglandins and, in particular, prostaglandin E2 ("PGE2"). Prostaglandins are derived from the fatty arachidonic acid. However, other mediators also are derived from arachidonic acid that mediate chronic inflammation, including the leukotrienes. The initial step in the formation of both leukotrienes and prostaglandins is the release of arachidonic acid from cell membrane phospholipids by the action of the enzyme phospholipase A2. Subsequently the arachidonic acid is converted to prostaglandins by another enzyme called cyclooxygenase ("Cox") while the same time a different enzyme called lipoxygenase converts arachidonic acid to leukotrienes.

Prostaglandins are a group of hormone-like chemicals which in tiny amounts have profound effects in stimulating and regulating various physiological processes in the body. PGE2 is of particular interest as elevated levels of PGE2 mediates inflammation in tissues and causes pain in the process by interacting with nerve cells. The key step in the formation of PGE2 is conversion of the fatty acid arachidonic acid to PGE2. This conversion step is regulated by the Cox enzyme. Cox is found in two subtypes called Cox-1 and Cox-2. Cox-1 is normally expressed in most tissues throughout the body and regulates blood flow in the kidneys, supports normal platelet aggregate function, and maintains the stomach lining through physiologic production of prostaglandins in the gastric mucosa.

Inflammation plays an important role in diseases as apparently diverse as cardiovascular disease, cancer, diabetes, osteoporosis, arthritis, Alzheimer's disease, and auto-immune diseases. In addition, inflammation plays a role in leaky gut syndrome in production animals. Bacteria can cause inflammation in the gut that can be reduced by anti-inflammatories. Stress can also cause inflammation of the gut. Stress can be from multiple sources including shipping livestock, nutrition, environmental changes, genetics or other unknown reasons.

Digestion and absorption of nutrients are the major roles for the intestines, as well as the prevention against the entry of antigens and microorganisms into the blood. However, the impairment of the intestinal barrier function and its increased permeability ("leaky gut") can lead to poor performance and disease. The intestinal barrier is mainly constituted by a single layer of epithelial cells, including enterocytes, goblet cells, Paneth cells, enteroendocrine cells, and immune cells. The cohesion between these cells and, thus, the regulation of the intestinal permeability is ensured by a dynamic protein complex called "tight junctions." The interaction between its physical, physiological, and immunological components enables a balanced permeability, providing an effective defense to macromolecules, bacterial products, and food antigens, but allowing a small fraction of molecules to cross the tight junctions and facilitating the coexistence with the intestinal microbiota without causing any harm. Effective prevention of leaky gut syndrome with natural anti-inflammatoires can be a goal to increase growth promotion in production animals.

Several factors including stress and inflammation have been identified to break down the intestinal barrier, thus increasing intestinal permeability and allowing the entry of macromolecules and endotoxins, which causes the activation of the immune system. Furthermore, the subsequent immune response suppresses appetite and redirects energy and nutrients towards the immune response and away from production purposes. An activated immune system requires large amounts of energy and nutrients that could otherwise be used for growth. It is estimated that the mucosal immune response can cost up to 30% in detriment of growth.

Moreover, stress associated with weaning and high ambient temperatures, for instance, are known to activate inflammatory cells to produce pro-inflammatory cytokines, which have deleterious effects on the intestinal morphology, compromising the intestinal barrier integrity.

Therefore, there is a need to develop strategies to minimize productivity losses when physiological states or environmental conditions activate the immune system and when inflammation of the gut occurs due to various reasons.

Alternatives to Antibiotics

Antimicrobial growth promoters have traditionally been antibiotics added to the feed of food animals to enhance their growth rate and production performance. It is estimated that over one-half of the antibiotics produced and sold in the United States have been used as a feed additive. They have been used because they have actually worked to enhance growth in production animals. However, in January of 2017, the US Food and Drug Administration (FDA) issued The Veterinary Feed Directive (FDA 2017) regarding the use of antibiotics in animals, which has effectively limited the use of antibiotics in the USA for growth promotion. This is due to the rise of antibiotic-resistant bacteria and associated problems for humans that need these antibiotics to be effective. Therefore, a challenge is to find agents that work like antibiotics for growth promotion but do not cause the associated problems. A further goal in effective production management may be using feeding strategies that also limit intestinal inflammation and promote gut health to improve growth performance and ensure the profitability of the animal production system.

For example, in pigs, porcine epidemic diarrhea virus (PEDV) is a coronavirus, associated with diarrhea in all ages of swine, and was first identified in 2013 in North America. Since then the virus has rapidly spread with over 8,560 positive cases in 31 states as of October 2014. Other diseases causing neonatal diarrhea and post-weaning diarrhea are caused by pathogenic bacteria and viruses including Enterotoxigenic *E. coli* (ETEC), and rotavirus. Similarly, *Brachyspira* and *Lawsonia* species represent the most important causes of bacterial enteric diseases of grow/finish pigs in the US. *L. intracellularis* causes porcine proliferative enteropathy and *B. hyodysenteriael B. hampsonii* are the etiologic agents of swine dysentery. Therefore, effective prevention and control of enteric diseases is critical to maintain production efficiency, produce wholesome pork, enhance food security and safety, and animal well-being. Biosecurity, treatment, and prevention strategies are needed to diminish economic losses associated with these various diseases without necessarily resorting to drugs and antibiotics.

By way of another example, in cattle, scours is a diarrheal disease that is a major cause of death in newborn calves. Calves are at highest risk during the first week of life gradually dropping after four weeks. Calves that do not die from scours may be faced with a negative energy balance resulting in fat and carbohydrate malabsorption. Damage to intestinal epithelium with subsequent villous atrophy is assumed to be the mechanism responsible for malabsorption. Surviving female calves will produce a lower lifetime milk yield and tend to be culled at a younger age than healthy cows. Scours is caused by a number of infectious agents including bacteria, such as *Escherichia coli* (*E. coli*) K99 and *Salmonella* species, viruses such as Rotavirus, Coronavirus, and Torovirus, and other pathogens such as Coccidia and *Cryptosporidium* species. The metabolic change resulting from etiologic organisms causing scours are similar. They include: 1) dehydration, 2) acidosis, 3) electrolyte abnormalities/imbalance and 4) negative energy balance and or hypoglycemia.

Another bovine enteric disease causes diarrhea due to coccidiosis. Three species of coccidia of most concern in cattle are *Eimeria bovis, E. zuernii*, and *E. auburnensis*. Infected animals must be treated for the infection and to correct dehydration. That treatment is typically carried out with drugs such as amprolium or ionophores or sulfa drugs. However, the efficacy may be reduced since resistance to anticoccidial drugs is now occurring. A preferable method would be to prevent the disease in the first place by using a natural feed additive that can reduce the presence of coccidia.

Enteric disorders in poultry can be a challenge to prevent and treat, since multiple pathogens are often involved and many diseases present with similar clinical signs, including stunted or abnormal growth, poor feed conversion, increased water intake, diarrhea, and enteritis (inflammation of the intestinal tract). Mortality rates vary widely. Sub-clinical disease is common and may still adversely affect production parameters. Important poultry enteric pathogens include *Salmonella*, reovirus, rotavirus and *E. coli* infections. Coccidiosis is the most common protozoal disease in poultry and a top contender for annual economic loss in the poultry industry. Protozoa *Eimeria* species cause reduction of production, malabsorption of nutrients, and mortality in chickens. *Eimeria tenella* is one of the most infectious and virulent protozoa found in chickens. To avoid an enormous loss, most farms follow anti-protozoal remedies including usages of coccidiostat to control protozoal infections. However, an efficacious, natural alternative to pharmaceutical coccidiostats has remained undiscovered.

The foregoing problems of efficient animal production create a need to provide alternatives to antibiotics for growth promotion and feed efficiency, as well as processes for creating such alternatives. The present invention describes a novel method that helps improve feed efficiency while reducing inflammation of the gut and results in improved gain and overall health in production animals.

Humans and Companion Animals

Companion animals such as dogs and cats play an important role in modern society, enhancing the psychological and well-being of many people. However, there are well-documented health risks associated with human animal interactions. More specifically, enteric pathogens of zoonotic risk which are transmitted by feces of dogs and cats can be grouped as follows: (a) Parasites such as *Toxocara canis, T. cati, Ancylostoma* sp., *Uncinaria* sp., *Strongyloides stercoralis, Echinococcus granulosus, E. multilocularis*, and *Dipylidium caninum* (b) Protozoa including *Toxoplasma gondii, Giardia duodenalis*, and *Cryptosporidium* spp. (c) Bacteria of the genera *Clostridium, Campylobacter, Salmonella, Escherichia, Yersinia*, and *Helicobacter* and (d) Viruses, mainly Rotaviruses and Coronaviruses. The use of a safe natural antimicrobial feed additive to the food of these companion animals may help reduce the incidence disease transmittance to the owner.

Humans suffer multiple problems from various enteric diseases. Enteric infections, with or without overt diarrhea, have profound effects on intestinal absorption, nutrition, and childhood development as well as on global mortality. Oral rehydration therapy has reduced the number of deaths from dehydration caused by infection with an enteric pathogen, but it has not changed the morbidity caused by such infections. The cost of the vicious cycle of enteric infections and malnutrition and their potential lasting impact is so great that multiple approaches must be taken to interrupt the cycle.

The foregoing problems due to enteric diseases in companion animals as well as in humans create a need, therefore, to provide additional processes for creating alternatives to antibiotics to combat enteric diseases and maintain a healthy gut microbiome. The present invention creates alternatives to antibiotics by a novel method that helps maintain a healthy gut microbiome while reducing inflammation of the gut. This helps maintain the health of both companion animals and humans that afflicted with enteric diseases.

Oral Rehydration Solutions

Enteric diseases often result in diarrhea. The use of oral rehydration solutions (ORS) containing electrolytes have been used to treat diarrhea in both humans and in mammals. ORS formulations include electrolytes of sodium chloride, sodium citrate, potassium chloride, and glucose. Glucose may be replaced by sucrose, and sodium citrate may be replaced by sodium bicarbonate. By replenishing electrolytes through uptake mechanisms in the intestinal villi, water will subsequently follow and help the human or animal rehydrate. However, ORS therapy does not kill the enteric pathogenic organisms and/or diseases that caused the diarrhea in the first place. An advance in the use of ORS would be to add antimicrobial and anti-inflammatory agents to kill the enteric pathogens and fight inflammation of the GI tract.

The current invention can be used in conjunction with ORS to provides electrolytes while concurrently providing antimicrobial and anti-inflammatory actions in the GI tract, thus improving the health of the human or animal.

SUMMARY OF THE INVENTION

The present invention is an oral ingestible composition for maintaining and improving health in animals affected by enteric diseases. The oral ingestible composition comprises a plurality of active ingredients in a dosage form, among them an iron-binding glycoprotein and at least one additional active ingredient.

The present invention also includes a method for maintaining and improving health in an animal affected by enteric disease by maintaining and improving the gut microbiome of the animal. This method includes administering the above oral ingestible composition to the animal.

The objects and advantages of the invention will appear more fully from the following detailed description of the embodiments of the invention and examples.

DETAILED DESCRIPTION OF THE INVENTION

Abbreviations

Unless otherwise noted, the following abbreviations will apply throughout this disclosure:
Cox: cyclo-oxygenase
GLA: gamma linolenic acid
IBD: inflammatory bowel disease
PGE2: prostaglandin E2
ROS: reactive oxygen species
SOD: super oxide dismutase Overview The present invention in a preferred version is a combination of powdered actives that contains an iron-binding glycoprotein and at least one additional active ingredient. One exemplary, non-limiting form of the invention comprises ovotransferrin as an iron-binding glycoprotein and chitosan as an additional active ingredient. The present invention can also contain alternative or additional active ingredients, such as *Curcumin* for additional anti-inflammatory activity. In one embodiment, the powder is mixed into animal feeds and is intended as a supplement to increase animal overall heath and gain by eliminating pathogenic micro-organisms in the gastrointestinal tract, stimulating the immune system and decreasing inflammation. In this sense it is an alternative to antibiotics that are commonly given to production animals to increase weight gain but goes beyond just being an antimicrobial. The current invention also reduces symptoms of inflammation in the gut while helping to maintain the gut microbiome when enteric diseases occur. The ingredients of the invention can also be incorporated into animal feed pellets either through mixing with the feed prior to extrusion of the pellets. The ingredients of the invention may also be sprayed onto pellets as a coating after pellet extrusion. This also advances the art of creating alternatives to antibiotics for production animals by allowing multiple delivery schemes of the invention. The invention uses a combination of active ingredients to stimulate the immune system while fighting inflammation and having antimicrobial activity in the GI tract of mammals.

The present invention can also be formulated into pharmaceutical forms, such as capsules and tablets, or other delivery systems, such as food products, for human use. The combination of the ingredients of the current invention allows for increased gut health. The product is intended as a feed supplement for mammals and as a nutraceutical supplement for humans to support a wide range antioxidant activity, antimicrobial, and anti-inflammation processes. There are many advantages to the method of this invention for administering anti-inflammation and antimicrobial agents. The manufacturing process also allows inclusion of other compounds such as, but not limited to, vitamins and minerals.

Any amounts disclosed herein are provided on a weight basis unless explicitly indicated otherwise or the context clearly indicates otherwise. For example, amounts provided as % are % w/w. Amounts provided as ratios are ratios by weight.

The amounts of each of the components in the composition may be varied from the amounts described herein depending upon the nature of the delivery drug, the weight and condition of the animal to be treated, and the unit dosage desired. Those of ordinary skill in the art will be able to adjust dosage amounts as required.

"Dosage form," as used generally herein, refers to a form of the composition that contains the active ingredients in absolute or relative amounts to obtain a one or more effects. Various dosage forms include capsules, tablets, dry powders, solutions, pastes, gels, feed compositions and feed coatings. The capsules, tablets, pastes, solutions, gels, feed compositions, and feed coatings, can be generated from a dry powder form of the composition. For example, the solution can be generated by mixing the powder with at least one liquid. The feed compositions can be generated by mixing the capsules, tablets, dry powders, pastes, solutions, or gels with animal feeds. The feed coatings can be generated by coating the capsules, tablets, dry powders, pastes, solutions, or gels onto animal feed.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

Anti-Microbials

A challenge facing the production animal industry is finding alternatives to antibiotics for growth promotion. Natural anti-microbials are required that do not cause bacteria resistance but are still effective. There are some natural antimicrobials available that help fill requirements as a growth promoter. These include the iron-binding glycoprotein ovotransferrin and the poly-glucosamine molecule chitosan.

Iron-Binding Glycoproteins Iron-binding glycoproteins are carrier proteins and metalloproteins that are important in iron metabolism and the immune response. Iron is required for life in varying amounts. Iron-binding glycoproteins are found in the blood of animals and other sources. For example, transferrin is found in blood and iron is needed by a cell, it is brought into the cytosol by a transferrin receptor. Lactoferrin is a member of the transferrin family and is the predominant protein found in mammal exocrine secretions, such as tears, milk, and saliva.

One iron-binding glycoprotein is ovotransferrin (also known as conalbumin), a protein found in eggs. 12%-13% of the total egg white protein is ovotransferrin. It is a member of the transferrin family, a group of ion-binding proteins with an in vivo preference for iron. Ovotransferrin consists of two lobes, each capable of binding one atom of $Fe^{3+}$ and carbonate anion. Among the two, the N-lobe is found to be more important for its antioxidant properties. Ovotransferrin was reported to possess super oxide dismutase-like activity against superoxide anion promoted by metal binding. The scavenging activity was dose-dependent and considerably higher than known for antioxidants such as ascorbate or serum albumin. Additionally, the iron-binding ability of ovotransferrin has an indirect role in preventing iron-induced lipid peroxidation.

Among the several protective functions of ovotransferrin, the most important one is likely to be the antibacterial activity, which is directly related to the ovotransferrin ability to bind iron ($Fe^{3+}$), making it unavailable for bacterial growth. The most sensitive species to the iron deprivation effect of ovotransferrin are *Pseudomonas* spp., *Escherichia coli*, *Streptococcus mutans*. *Proteus* spp., and *Klebsiella* spp. are less sensitive. Part of the antibacterial activity of ovotransferrin may not simply be due to the removal of iron from the medium, but also may involve more complex mechanisms related to a direct binding of ovotransferrin to the bacterial surface. Ovotransferrin is able to permeate the *E. coli* outer membrane and access the inner membrane, causing both ion leakage inside bacteria and the uncoupling of the respiration-dependent energy production thus killing the bacteria. Ovotransferrin also has antiviral activity although that activity does not seem to be related to it iron-binding capability.

Iron-binding glycoproteins such as transferrin, ovotransferrin, lactoferrin, and ferritin can be purified by standard methods in the art into powders. The iron-binding glycoproteins can also be solubilized. The iron-binding glycoprotein as a powder can be mixed with the other actives of the invention and delivered to an animal when mixed into dry feeds. The soluble form of the iron-binding glycoprotein can be delivered through watering systems to deliver to animals or mixed into pastes or gels and delivered.

The amount of iron-binding glycoprotein in the oral ingestible composition can range from 0.01% to 95%.

In some versions of the invention, the oral ingestible composition comprises the iron-binding glycoprotein in an amount of at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some versions of the invention, the oral ingestible composition comprises the iron-binding glycoprotein in an amount up to about 0.1%, up to about 0.2%, up to about 0.3%, up to about 0.4%, up to about 0.5%, up to about 0.6%, up to about 0.7%, up to about 0.8%, up to about 0.9%, up to about 1%, up to about 1.5%, up to about 2%, up to about 3%, up to about 4%, up to about 5%, up to about 6%, up to about 7%, up to about 8%, up to about 9%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, or up to about 95% by weight.

Chitosan

Chitosan is a non-toxic polyglucosamine, widespread in nature, which is deacetylated to varying degrees from chitin, a component of exoskeleton of shrimps, crabs and insects. Chitosan is a linear polysaccharide composed of randomly distributed ß-linked D-glucosamine and N-acetyl-D-glucosamine. Chitosan has antimicrobial, anti-inflammatory, anti-oxidative, antitumor, immunostimulatory and hypocholesterolemic properties when fed as a dietary additive for animals. These effects may at least in part result from its reactive functional groups, that is, amino acids and hydroxyl groups. In poultry (e.g., broiler chickens) and pigs (e.g., weaned pigs), in particular, chitosan has beneficial, biological effects, including immunomodulatory, anti-oxidative, antimicrobial and hypocholesterolemic effects. The effects of chitosan can be reflected in improved growth performance (body weight gain and/or feed conversion ratio) of young animals. Chitosan's antimicrobial action may come from binding of chitosan to teichoic acids in bacteria coupled with a potential extraction of membrane lipids (predominantly lipoteichoic acid), ultimately leading to bacterial death.

The amount of chitosan in the oral ingestible composition ranges from 0.01% to 95%.

In some versions of the invention, the oral ingestible composition comprises the chitosan in an amount of at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some versions of the invention, the oral ingestible composition comprises the chitosan in an amount up to about 0.1%, up to about 0.2%, up to about 0.3%, up to about 0.4%, up to about 0.5%, up to about 0.6%, up to about 0.7%, up to about 0.8%, up to about 0.9%, up to about 1%, up to about 1.5%, up to about 2%, up to about 3%, up to about 4%, up to about 5%, up to about 6%, up to about 7%, up to about 8%, up to about 9%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, or up to about 95% by weight.

Phytobotanical Anti-Inflammatories

An approach of the current invention as a growth promoter for production animals is to include an anti-inflammatory agent. The anti-inflammatory agents can be of an herbal/phytobotanical nature. Certain herbs have been found to be highly beneficial to fight inflammatory conditions as they contain specific compounds that are biologically active. For example, turmeric (*Curcumin longa*) that contains *Curcumin*, garlic (*Allium sativum*), cinnamon (*Cinnamonum* spp.), ginger, (*Zingiber officianale*), Roman chamomile, *Echinacea*, red clover, goldenseal, Vitex (Chaste tree), black pepper, and clove are among the phytobotanicals that have anti-inflammatory activity that can be effective in the invention.

The amount of phytobotanical anti-inflammatory agent in the oral ingestible composition can range from 0.01% to 50%.

In some versions of the invention, the oral ingestible composition comprises the phytobotanical anti-inflammatory agent in an amount of at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some versions of the invention, the oral ingestible composition comprises the phytobotanical anti-inflammatory agent in an amount up to about 0.1%, up to about 0.2%, up to about 0.3%, up to about 0.4%, up to about 0.5%, up to about 0.6%, up to about 0.7%, up to about 0.8%, up to about 0.9%, up to about 1%, up to about 1.5%, up to about 2%, up to about 3%, up to about 4%, up to about 5%, up to about 6%, up to about 7%, up to about 8%, up to about 9%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, or up to about 95% by weight.

Curcumin

*Curcumin* is the active ingredient of turmeric. It is widely used as a safe kitchen spice and food colorant throughout the world. It is a complex molecule with multiple biological targets and different cellular effects. *Curcumin* has anti-inflammatory, antioxidant and anti-cancer properties. *Curcumin* is a yellow pigment and an active ingredient from turmeric that is typically found in most curry food. The FDA classified turmeric among substances "generally recognized as safe." *Curcumin* exhibits potent anti-inflammatory and analgesic effects in animals and humans. *Curcumin* inhibits Cox-2 activity in a number of gastrointestinal cell lines including colon, esophagus and small intestine. *Curcumin* is able to inhibit Cox-2 selectively without inhibiting Cox-1 expression. This may be due to *Curcumin* targeting the gene that codes for Cox-2 and hence decreases the amount of the enzyme present. This ability to selectively inhibit Cox-2 expression and activity may account for the lack of gastrointestinal side effects and being safe despite being an anti-inflammatory agent.

In some versions of the invention, the oral ingestible composition comprises the *Curcumin* in an amount of at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.5%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% by weight. In some versions of the invention, the oral ingestible composition comprises the *Curcumin* in an amount up to about 0.1%, up to about 0.2%, up to about 0.3%, up to about 0.4%, up to about 0.5%, up to about 0.6%, up to about 0.7%, up to about 0.8%, up to about 0.9%, up to about 1%, up to about 1.5%, up to about 2%, up to about 3%, up to about 4%, up to about 5%, up to about 6%, up to about 7%, up to about 8%, up to about 9%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%, up to about 85%, up to about 90%, or up to about 95% by weight.

Amounts of Components

The amounts of each of the components in the final product composition may be varied depending upon the nature of the composition, the weight and condition of the animal to be treated, and the unit dosage desired. Those of ordinary skill in the art will be able to adjust dosage amounts as required.

Exemplary ratios of the ovotransferrin, chitosan, and *Curcumin* in the compositions of the invention on a weight to weight basis can be 1:1:1 (ovotransferrin:chitosan:*Curcumin*). Other ratios can be applied, depending on the desired antimicrobial and anti-inflammatory activity required in different circumstances. Bulking agents can be added to the composition as required to make weighing and use of the product more practical in different situations.

Delivery into Feeds

In feed dosage forms, the composition of the invention can be mixed into animal feeds simply by weighing desired amounts of the complete composition into powdered feed mash and then thoroughly mixing together by methods known in the art. The feed containing the composition can then delivered to animals to consume in feed troughs. The composition of the invention can be mixed into dough that is extruded for animal feed pellets. The composition of the invention may also be added to or diluted into water. The animal can then consume the composition through drinking water and can also be delivered through drinking water piping systems. Furthermore, the composition of the invention can be mixed into water and then sprayed onto pellets after the pellet extrusion process using methods known in the art. Non-limiting examples of suitable animal feeds include feeds for poultry, dogs, cats, horses, cattle, pigs, goats, and sheep.

Delivery into Capsules and Tablets

The composition of the invention can also be manufactured in pharmaceutical forms such as, but not limited to, capsules or tablets using standard methods in the industry. The dosage amounts to use can be determined on a case by case basis. These capsules and tablets can be given to humans as a nutraceutical supplement to improve the microbiome and maintain gut health.

PREFERRED EMBODIMENTS OF THE INVENTION

Preferred compositions of the invention are in a powder form.

The powder composition preferably comprises an iron-binding glycoprotein. The powder composition more preferably comprises an iron-binding glycoprotein and one or more of chitosan and a phytobotanical anti-inflammatory agent.

In powder compositions comprising an iron-binding glycoprotein, the iron-binding glycoprotein preferably constitutes at least about 50% by weight, at least about 55% by weight, at least about 60% by weight, at least about 65% by weight, at least about 70% by weight, at least about 75% by weight, at least about 80% by weight, at least about 85% by weight, at least about 90% by weight, at least about 91% by weight, at least about 92% by weight, at least about 93% by weight, at least about 94% by weight, at least about 95% by weight, at least about 96% by weight, at least about 97% by weight, at least about 98% by weight, or at least about 99% by weight of the powder composition.

In powder compositions comprising the iron-binding glycoprotein and one or more of chitosan and the phytobotanical anti-inflammatory agent, the iron-binding glycoprotein and the one or more of the chitosan and the phytobotanical anti-inflammatory agent together preferably constitute at least about 50% by weight, at least about 55% by weight, at least about 60% by weight, at least about 65% by weight, at least about 70% by weight, at least about 75% by weight, at least about 80% by weight, at least about 85% by weight, at least about 90% by weight, at least about 91% by weight, at least about 92% by weight, at least about 93% by weight, at least about 94% by weight, at least about 95% by weight, at least about 96% by weight, at least about 97% by weight, at least about 98% by weight, or at least about 99% by weight of the powder composition. In some of these compositions, the one or more of the chitosan and the phytobotanical anti-inflammatory agent consist of chitosan. In some of these compositions, the one or more of the chitosan and the phytobotanical anti-inflammatory agent consist of the phytobotanical anti-inflammatory agent. In some of these compositions, the one or more of the chitosan and the phytobotanical anti-inflammatory agent consist of the chitosan and the phytobotanical anti-inflammatory agent.

The iron-binding glycoprotein is preferably present in the powder composition in an amount of at least about 15% by weight of the powder composition. The chitosan is preferably present in the powder composition in an amount of at least about 15%. The phytobotanical anti-inflammatory agent is preferably present in the powder composition in an amount of at least about 5% by weight of the powder composition.

Various preferred glycoprotein:chitosan:phytobotanical anti-inflammatory agent weight ratios present in the powder composition include about 1:1:1, about 2:2:1, and about 2:7:1.

The iron-binding glycoprotein is preferably selected from a transferrin and a ferritin. Proteins in the transferrin family and the ferritin family are well known in the art. See, e.g., Lambert et al. 2005 (Lambert L A, Perri H, Halbrooks P J, Mason A B. Evolution of the transferrin family: conservation of residues associated with iron and anion binding. Comp Biochem Physiol B Biochem Mol Biol. 2005 October; 142(2): 129-41) for a review of the transferrin family. See, e.g., Theil 1990 (Theil E C. The ferritin family of iron storage proteins. *Adv Enzymol Relat Areas Mol Biol.* 1990; 63:421-49) for a review the ferritin family. Preferred transferrins include ovotransferrin, transferrin, and lactoferrin. A particularly preferred transferrin includes ovotransferrin.

Preferred phytobotanical anti-inflammatory agents include *Curcumin* (*Curcumin longa*, also known as turmeric), garlic (*Allium sativum*), cinnamon (*Cinnamonum* spp.), ginger, (*Zingiber officianale*), Roman chamomile, *Echinacea*, Red clover, goldenseal, Vitex (Chaste tree), black pepper, and clove. A particularly preferred phytobotanical anti-inflammatory agent is *Curcumin*.

The powder composition can be mixed with a consumable to form a supplemented consumable. "Consumable" is used herein to refer to any substance capable of being orally consumed by an animal. Exemplary consumables include food, animal feed, rehydration solutions, and water. In various versions, the supplemented consumable comprises the composition of the invention in an amount of at least about 0.001% by weight, at least about 0.01% by weight, at least about 0.1% by weight, at least about 0.5% by weight, at least about 1% by weight, at least about 1% by weight, at least about 2% by weight, at least about 3% by weight, at least about 4% by weight, at least about 5% by weight, at least about 6% by weight, at least about 1% by weight, at least about 8% by weight, or at least about 9% by weight. In various versions, the supplemented consumable comprises the composition of the invention in an amount less than about 0.1% by weight, less than about 0.5% by weight, less than about 1% by weight, less than about 1% by weight, less than about 2% by weight, less than about 3% by weight, less than about 4% by weight less than about 5% by weight, less than about 6% by weight, less than about 1% by weight, less than about 8% by weight, less than about 9% by weight, or less than about 10% by weight. Preferred supplemented consumables comprise the composition of the invention in an amount between about 0.1% to about 10% by weight. The form of the composition can change from powder to another form depending on the consumable with which it is mixed and the manner in which it is mixed with the consumable.

The supplemented consumable is preferably orally administered to an animal in an amount effective to obtain any of a number of effects. Such effects include but are not limited to weight gain, an increase in gut microbiome diversity, and prolonged survival. Such effects are determined relative to orally administering the consumable without supplementation with the composition of the invention. The animal can be an animal with a pathogenic microbial infection. Exemplary pathogenic microbial infections include bacterial infections, viral infections, protozoal infections, fungal infections, and combinations thereof. The animal can be an animal with an infection with an enteric pathogen. Exemplary enteric pathogens include any enteric pathogen described herein. The animal can be an animal with an enteric disease. Exemplary enteric diseases include any enteric disease described herein.

EXAMPLES

Example 1

Ovotransferrin was purified from chicken egg whites and ground into a powder. Powdered components (ovotransferrin, chitosan and *Curcumin*) of the invention were mixed together in equal amounts to create a powder of the invention. The powder of the invention was mixed into chicken feed mash by adding 27 grams of powder per 5 lbs of mash to create a treatment feed. One day old chickens (N=32) were given treatment feed ad libitum on a daily basis over the course of a 4-week trial. One day old chickens (N=16) were given control feed over the same 4-week period. Control and treatment groups were in identical pens with 2 square foot available to all birds. Weights of birds were taken on weekly basis and amount of feed consumed was measured in both groups. Feed Efficiency was calculated based on amount of average feed consumed per bird per average weight of bird. The results are in Table 1.

TABLE 1

| Day | Ave bird weight of control (g) | Ave bird weight of treatment (g) | Feed Efficiency of control | Feed Efficiency of treatment |
|---|---|---|---|---|
| 1 | 41.8 | 40.2 | | |
| 7 | 161.6 | 165.5 | 2.19 | 1.88 |
| 14 | 343.0 | 281.3 | 1.76 | 1.26 |
| 21 | 597.5 | 684.2 | 1.39 | 0.75 |
| 28 | 1042.6 | 1075.9 | 1.161 | 0.72 |

Results: The treatment birds on average had an increased weight relative to the control birds especially after 2 weeks. In addition, the feed efficiency of the treatment birds was better than the control birds. These results are consistent with ovotransferrin of the invention being efficacious as a growth promoter and being alternative to antibiotics.

Example 2

Ovotransferrin was purified from chicken egg whites into a dried powder. Powered components of the invention were mixed together as described in example 1. The powder of the invention was mixed into chicken mash by adding 27 grams of powder per 5 lbs of mash to create a treatment feed. Forty-two-day old chickens (N=17) were given treatment feed ad libitum on a daily basis over the course of a one-week trial. Forty-two-day old chickens (N=17) were given control feed over the same week period. Control and treatment groups were in identical pens with 2 square foot available to all birds. Weights of birds were taken on day 49 and relative gain was determined between the treatment and the control group.

Results: The average treatment group gained relatively more weight than the control group and weighed considerably more (Treatment has a 19% coefficient of variation (CV) and the Control group has a 16% CV), despite the initial average weight of the treatment birds being less than the control birds. These results are consistent with ovotransferrin of the invention as being efficacious in older birds as a growth promoter. The results are seen in Table 2.

TABLE 2

| | Relative Bird weight Gain | | |
|---|---|---|---|
| | Ave Bird weight (g) on Day 42 | Ave Bird weight (g) on day 49 | Relative Gain |
| Treatment | 2006.4 | 2705.1 | 1.34 |
| Control | 2216.2 | 2512.9 | 1.13 |

Example 3

Protozoa species cause reduction of production, malabsorption of nutrients, and mortality in chickens. *Eimeria tenella* is one of the most infectious and virulent protozoa found in chickens that causes coccidiosis. The objective of this example was to determine the effects of ovotransferrin and chitosan on growth performance including feed conversion rate and inhibition of *E. tenella* infection in broiler chickens. Ovotransferrin was purified from chicken egg whites into a dried powder. Chitosan powder was commercially purchased. Day-old chickens (n=125) were housed in standard conditions and randomly divided into groups. Water and commercially available same feeds were given as basal diets (BD) to all birds. Different percentages of ovotransferrin and chitosan (0.5%, 1%, and 2% alone or combined) were mixed with feed and given from day 7 through 21 to the treated groups while the control groups received starch. Approximately 106 numbers of sporulated *E. tenella* oocysts were administered orally at day 14 to treated groups. Body weight and feed intake were determined, oocysts in the feces were counted and cecum samples were collected while birds were sacrificed at the end of the experiments. Histopathology was performed for all collected cecum samples.

Results: The infection by *E. tenella* caused body weight to decrease compared to the control animals. However, body weight was increased in both ovotransferrin and chitosan treated groups as compared to control (Tables 3 and 4). Both ovotransferrin alone and chitosan alone inhibited *E. tenella* infection while body weight was significantly (*p<0.01) increased. The combined ovotransferrin with chitosan also to show increased body weight over the infected control animals that received no treatment (Table 5). Feed conversion rate was higher in both ovotransferrin and chitosan treated groups. Oocysts count in fecal sample was significantly lower (*p<0.01) in ovotransferrin and chitosan treated groups as compared with positive infected control. The histopathology also showed the normal structures of cecal epithelium, but not in positive infected control groups. We conclude that ovotransferrin and chitosan of the invention increase growth performance and inhibit coccidiosis in broiler chickens.

TABLE 3

Weight (g) in chickens infected with *E. tenella*.

| Day | Uninfected Control Animals | Infected Animals | Infected Animals but treated with 0.5% ovotransferrin |
|---|---|---|---|
| 7  | 117 ± 7  | 106 ± 5  | 110 ± 5  |
| 14 | 278 ± 14 | 267 ± 8  | 283 ± 10 |
| 21 | 381 ± 15 | 345 ± 22 | 470 ± 15 |

| Day | Uninfected Control Animals | Infected Animals | Infected Animals but treated with 1.0% ovotransferrin |
|---|---|---|---|
| 7  | 112 ± 6  | 114 ± 7  | 115 ± 6  |
| 14 | 268 ± 12 | 272 ± 18 | 293 ± 14 |
| 21 | 378 ± 15 | 357 ± 21 | 529 ± 22 |

| Day | Uninfected Control Animals | Infected Animals | Infected Animals but treated with 2.0% ovotransferrin |
|---|---|---|---|
| 7  | 114 ± 5  | 82 ± 6   | 115 ± 6  |
| 14 | 252 ± 11 | 252 ± 12 | 293 ± 14 |
| 21 | 374 ± 14 | 320 ± 22 | 571 ± 15 |

TABLE 4

Weight (g) in chickens infected with *E. tenella*.

| Day | Uninfected Control Animals | Infected Animals | Infected animals but treated with 0.5% chitosan |
|---|---|---|---|
| 7  | 114 ± 6  | 110 ± 5  | 78 ± 4   |
| 14 | 274 ± 9  | 270 ± 18 | 288 ± 12 |
| 21 | 380 ± 16 | 328 ± 16 | 467 ± 15 |

| Day | Uninfected Control Animals | Infected Animals | Infected Animals but treated with 1.0% chitosan |
|---|---|---|---|
| 7  | 108 ± 8  | 111 ± 7  | 112 ± 6  |
| 14 | 289 ± 12 | 289 ± 12 | 289 ± 12 |
| 21 | 384 ± 16 | 330 ± 18 | 502 ± 15 |

| Day | Uninfected Control Animals | Infected Animals | Infected Animals but treated with 2.0% chitosan |
|---|---|---|---|
| 7  | 98 ± 7   | 95 ± 4   | 93 ± 6   |
| 14 | 260 ± 12 | 258 ± 9  | 290 ± 18 |
| 21 | 376 ± 15 | 348 ± 14 | 541 ± 15 |

TABLE 5

Weight (g) in chickens infected with *E. tenella*.

| Day | Uninfected Control Animals | Infected Animals | Infected Animals but treated with 0.5% chitosan and 0.5% ovotransferrin |
|---|---|---|---|
| 7  | 117 ± 8  | 106 ± 4  | 110 ± 6  |
| 14 | 270 ± 14 | 272 ± 12 | 295 ± 16 |
| 21 | 381 ± 25 | 336 ± 24 | 476 ± 18 |

| Day | Uninfected Control Animals | Infected Animals | Infected Animals but treated with 1.0% chitosan and 1.0% ovotransferrin |
|---|---|---|---|
| 7  | 100 ± 6  | 99 ± 6   | 97 ± 8   |
| 14 | 262 ± 15 | 260 ± 12 | 260 ± 12 |
| 21 | 381 ± 18 | 357 ± 25 | 506 ± 18 |

TABLE 5-continued

Weight (g) in chickens infected with E. tenella.

| Day | Uninfected Control Animals | Infected Animals | Infected Animals but treated with 2.0% chitosan and 2.0% ovotransferrin |
|---|---|---|---|
| 7 | 104 ± 7 | 106 ± 5 | 100 ± 6 |
| 14 | 288 ± 8 | 268 ± 8 | 288 ± 10 |
| 21 | 381 ± 16 | 337 ± 26 | 517 ± 26 |

Example 4

Porcine epidemic diarrhea (PEDV) caused by coronavirus infection at pig production facilities result in diarrhea and typically ends in the death of pigs, if untreated. Oral rehydration solutions (ORS) are used to treat the diarrhea but are not very effective in preventing death. A dose response experiment was carried out with ovotransferrin of the invention being supplemented in the presence or absence of oral rehydration solutions to 25 newborn piglets diagnosed and confirmed with PEDV. Piglets that were judged to be equivalent in severity of the diarrhea and physical condition prior to the start of the experiment were randomly placed in 5 groups of N=5. Ovotransferrin was supplemented at 0, 1 and 5 grams into water or ORS and given as a 100 ml drench (forcible ingestion) twice daily over the course of 5 days. Diarrhea was measured on the basis of frequency of defecations per day.

TABLE 6

Dose response of ovotransferrin supplementation on PEDV survival in newborn piglets after 5 days.

| Grams of Ovotransferrin | % Survival |
|---|---|
| 0 | 40 |
| 2 | 40 |
| 5 | 60 |

TABLE 7

Dose response of ovotransferrin supplementation in conjunction with ORS therapy in PEDV survival in newborn piglet after 5 days.

| Grams of Ovotransferrin in Presence of ORS | % Survival |
|---|---|
| 0 | 40 |
| 2 | 80 |
| 5 | 100 |

TABLE 8

Defecations/day/group in newborn piglets with PEDV supplemented with ovotransferrin.

| Grams of Ovotransferrin | Day 0 | Day 1 | Day 3 | Day 5 |
|---|---|---|---|---|
| 0 | 30 | 22 | 20 | 20 |
| 2 | 30 | 18 | 14 | 12 |
| 5 | 26 | 18 | 15 | 12 |

TABLE 9

Defecations/day/group in newborn piglets with PEDV supplemented with ovotransferrin in conjunction with ORS therapy.

| Grams of Ovotransferrin in Presence of ORS | Day 0 | Day 1 | Day 3 | Day 5 |
|---|---|---|---|---|
| 0 | 30 | 22 | 20 | 20 |
| 2 | 28 | 18 | 15 | 14 |
| 5 | 30 | 15 | 10 | 10 |

The results in Table 6, not surprisingly, showed that PEDV results in the death of 60% of the piglets in this trial. However, ovotransferrin of the invention helped PEDV piglets to survive better. Table 6 shows efficacy of ovotransferrin to keep more piglets alive in a dose response manner. Surprisingly and unexpectantly, the results in Table 7 showed that when ovotransferrin was given in conjunction with ORS therapy, a synergistic response occurred that allowed for all the piglets to survive the PEDV infection. Consistent with the increased survival, Table 8 shows that ovotransferrin helps reduce the number of defecations that the piglets have over the course of the 5-day trial. This is also consistent with the idea that ovotransferrin is reducing PEDV infection and allows for better survival in the group. In Table 9 when ovotransferrin is used in conjunction with ORS therapy, further reduction of defections occurred in a dose dependent manner. This unexpected result is consistent with ovotransferrin in the invention helping overall gut health in mammals with enteric diseases such as PEDV, especially in conjunction with ORS therapy.

Example 5

Weaning can be a stressful time for performance animals that are transitioning to new food and newly encountering enteric pathogens. These factors can result in diarrhea to varying degrees. The objective of this study was to evaluate the effect of supplementing dietary ovotransferrin of the invention to pigs that had slight diarrhea within a week upon weaning. Growth performance and fecal score were measured. Within 1-7 days post weaning, a total of 54 pigs that exhibited diarrhea were assigned to 3 treatments in 18 replicates for a 28-d feeding trial. Pigs with diarrhea were housed in the nursery pens with 3 pigs per pen and allowed free access to the diet and water ad-libitum for the entire experimental period. Then, they were treated with a solution mixed with electrolytes and ovotransferrin by drenching for 3 days. Ovotransferrin was produced as described in example 1. The pigs were fed test diets containing 0, 0.5, and 1.0% ovotransferrin of the invention. Body weight were recorded at day 0 (study initiation), day 7, 14, 21, and 28 postweaning. Average daily gain (ADG), average daily feed intake (ADFI) and gain:feed (G:F) ratio were calculated weekly from day 7-28 postweaning. Corn-soybean meal-based diets were used for 28 days with 2 phases (Phase 1: day 0-14 postweaning and Phase 2: day 15-28 postweaning).

Ovotransferrin was added to the diets by replacing corn starch proportionally. Fecal score was recorded daily through day 14. Body weight and feed consumption were recorded weekly for the diarrhea pigs.

TABLE 10

Fecal score of pigs.

| Item | Ovotransferrin levels, % | | | SEM | P-values | |
|---|---|---|---|---|---|---|
| | 0 | 0.5 | 1 | | Linear | Quadratic |
| Fecal score | | | | | | |
| d 0-7 | 1.88 | 1.81 | 1.57 | 0.107 | 0.11 | 0.56 |
| d 7-14 | 1.71 | 1.79 | 1.64 | 0.100 | 0.64 | 0.43 |
| d 0-14 (Phase 1) | 1.80 | 1.80 | 1.61 | 0.068 | 0.12 | 0.31 |
| d 0-28 (Overall) | 1.70 | 1.68 | 1.58 | 0.067 | 0.27 | 0.68 |

≤1 = normal,
2 = slight diarrhea,
3 = moderate diarrheic feces, and
4 = liquid, severe diarrhea for each pen following observations of individual pig and signs of stool consistency in the pen.

Results: Fecal scores in Table 10 during d 0-7 (P=0.11) and 0-14 (P=0.12) postweaning tended to decrease with increasing ovotransferrin of the invention in supplementation levels from 0 to 1.0%. These results are consistent with hypothesis that ovotransferrin of the invention helps maintain the health of the gut in mammals during transitional times when enteric pathogens can be present.

TABLE 11

Growth performance of pigs.

| Item | Ovotransferrin levels, % | | | SEM | P-values | |
|---|---|---|---|---|---|---|
| | 0 | 0.5 | 1 | | Linear | Quadratic |
| Body weight, kg | | | | | | |
| d 7 | 7.92 | 7.87 | 7.61 | 0.118 | 0.14 | 0.51 |
| d 14 | 10.37 | 10.37 | 11.09 | 0.378 | 0.25 | 0.48 |
| d 21 | 13.92 | 14.33 | 15.18 | 0.945 | 0.40 | 0.86 |
| d 28 | 17.65 | 19.23 | 21.16 | 1.507 | 0.18 | 0.93 |
| ADG, g/d | | | | | | |
| d 7-14 | 349.57 | 356.06 | 496.75 | 57.678 | 0.15 | 0.40 |
| d 14-21 | 506.49 | 566.02 | 584.42 | 103.404 | 0.62 | 0.88 |
| d 21-28 | 533.55 | 700.22 | 853.90 | 98.053 | 0.08 | 0.96 |
| d 7-28 | 463.20 | 540.76 | 645.02 | 75.649 | 0.16 | 0.89 |
| ADFI, g/d | | | | | | |
| d 7-14 | 491.34 | 581.17 | 654.76 | — | — | — |
| d 14-21 | 927.49 | 933.98 | 1084.42 | — | — | — |
| d 21-28 | 984.85 | 1089.83 | 1390.69 | — | — | — |
| d 7-28 | 801.23 | 868.33 | 1043.29 | — | — | — |
| G:F | | | | | | |
| d 7-14 | 0.711 | 0.613 | 0.759 | 0.1072 | 0.77 | 0.40 |
| d 14-21 | 0.546 | 0.606 | 0.539 | 0.1039 | 0.96 | 0.64 |
| d 21-28 | 0.542 | 0.643 | 0.614 | 0.0837 | 0.57 | 0.56 |
| d 7-28 | 0.578 | 0.623 | 0.618 | 0.0801 | 0.74 | 0.81 |

Results: Table 11 shows there were linear increases with tendency in body weight at d 28 postweaning (P=0.18) and ADG in d 7-14 (P=0.15), d 21-28 (P=0.08), and d 7-28 (P=0.16) postweaning with increasing ovotransferrin supplementation levels from 0 to 1.0%. There were increases in the Pen ADFI with increasing ovotransferrin supplementation but no significant difference in Gain: Feed ratio. The results are consistent with the hypothesis that ovotransferrin of the invention can help improve weight gain in mammals that are experiencing diarrhea and are consistent with the efficacy of the ovotransferrin in the invention to improve gut health. These results are consistent with the use of the invention to ensure healthier and larger production animals, such as pigs, than without it.

Example 6

The microbiome of newly weaned piglets with diarrhea was examined when treated with components of the invention. Fecal samples of N=3 control (C) newly weaned piglets without diarrhea (D) and for N=6 newly weaned piglets that did have diarrhea were examined. 3 of these piglets with diarrhea were randomly selected and treated (T3) with 2.5 grams/piglet/day with ovotransferrin by mixing the ovotransferrin into dry feed for 5 consecutive days. Fecal samples were taken from the Diarrhea pigs, the Treated piglets and Control piglets after 5 days trial.

Fecal samples then had DNA was extracted using the PowerSoil DNA extraction kit (QIAGEN). Extracted DNA was then sequenced where the V4 variable region of the bacterial 16S rRNA gene was amplified (Primers 515F and 806R) and libraries constructed using a dual index approach1. 16SrRNA libraries were sequenced on a MiSeq V3 instrument (Illumina), targeting 2×300 PE reads. Bioinformatics occurred by processing of amplicons that was based on protocols that rely on several open-source software (FastQC2, cutadapt3, bbmap4 and the DADA25 plugin within QIIME26) to remove adaptors and primer sequences, merge PE reads, filter out low quality reads and generate counts of unique Amplicon Sequence Variants (ASVs) or unique taxonomic groups that represent the abundance of species and/or strains in each sample.

All statistical analyses, including multivariate and univariate methods were performed using various packages (labdsv, vegan, ape) in the R statistical interface. These analyses included alpha (Shannon index, observed ASVs) and beta diversity (Bray-Curtis distances visualized in Principal coordinate analyses (PCoA) plots) and estimation, and analyses of indicator species (indval). This analysis provides an indicator value for each ASV or species that reflects the frequency and abundance of each taxon in samples of a given group; the indicator value goes from 0-1 with the best indicators >0.5. After sequence quality control and bioinformatic processing, an average of 53,965+/−9,808 sequence reads per sample were obtained.

Figure 1A:
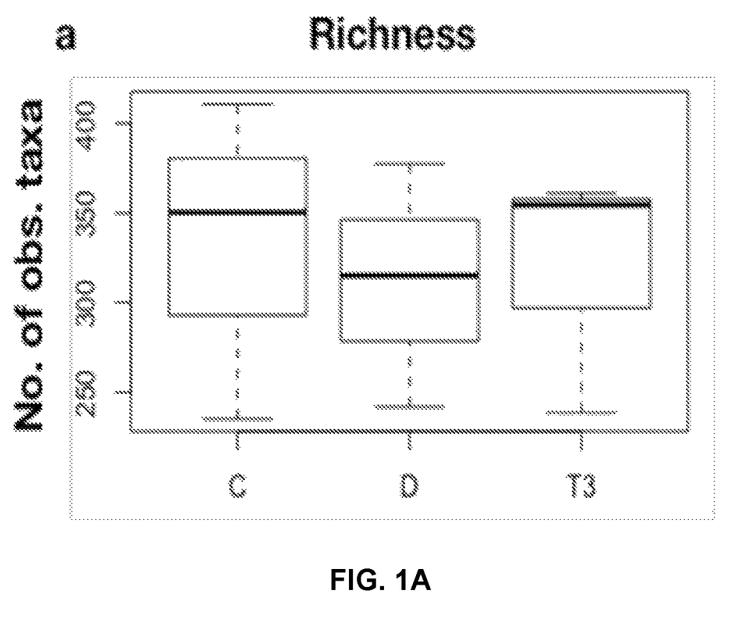
FIGS. 1A and 1B show alpha diversity analyses showing richness (number of different ASVs) and diversity (Shannon index), respectively, among samples from Healthy Control group (C), Diarrhea group (D) and Treatment group (T3).
Figure 1B:
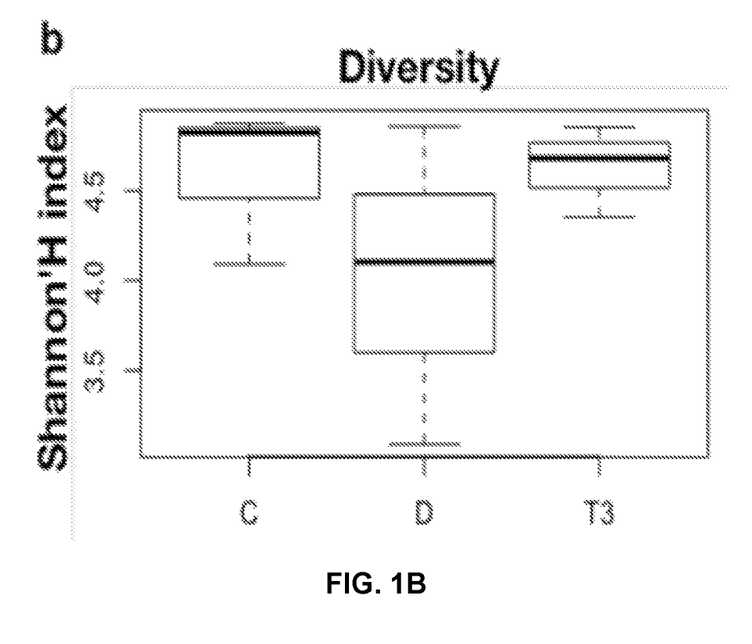
Figure 2:
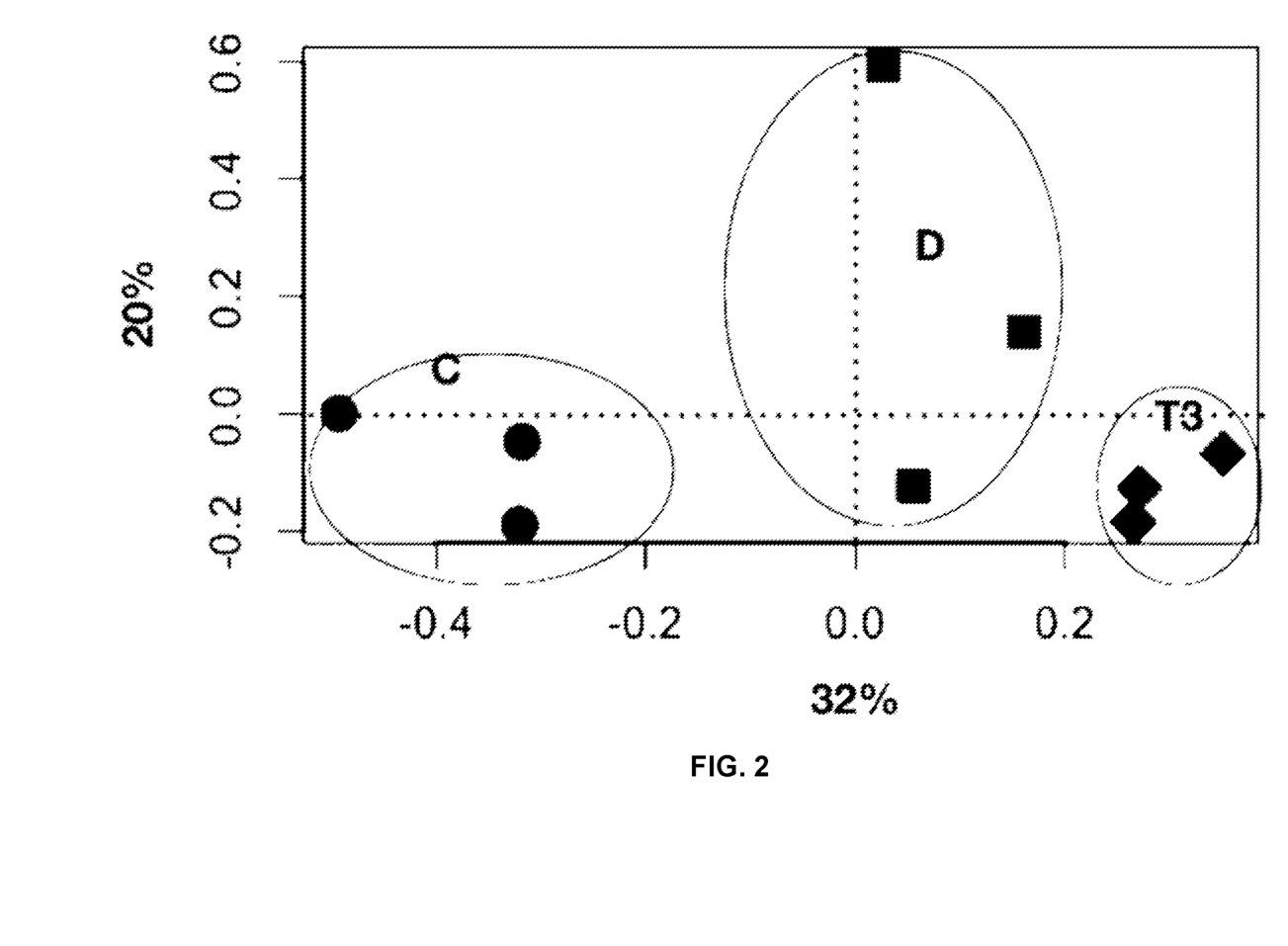
FIG. 2 shows a Bray-Curtis PCoA showing distinct gut bacterial communities among healthy Control group (C), Diarrhea group (D) and Treatment group (T3).
Figure 3A:
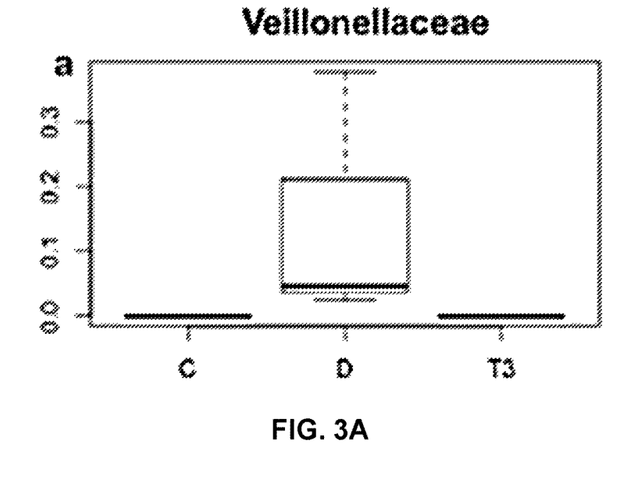
FIGS. 3A, 3B, 3C, and 3D show microbiome species differences between Veillonellaceae, Enterobacteriaceae, *Paraprevotellaceae*, and *Treponema* species, respectively, when diarrhea (D) occurs in piglets and when treated (T3) as compared to controls (C).
Figure 3B:
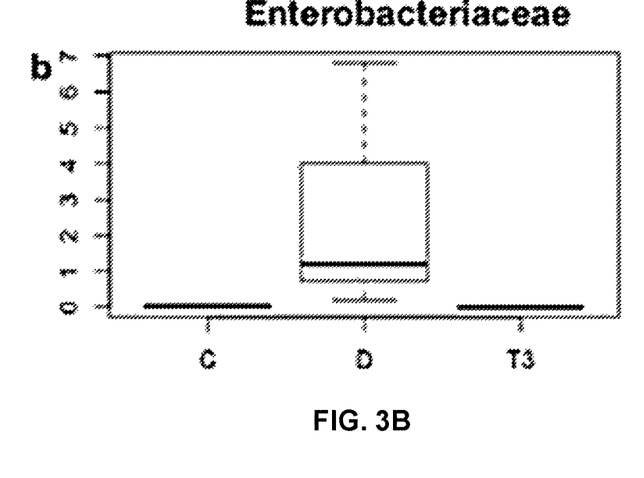
Figure 3C:
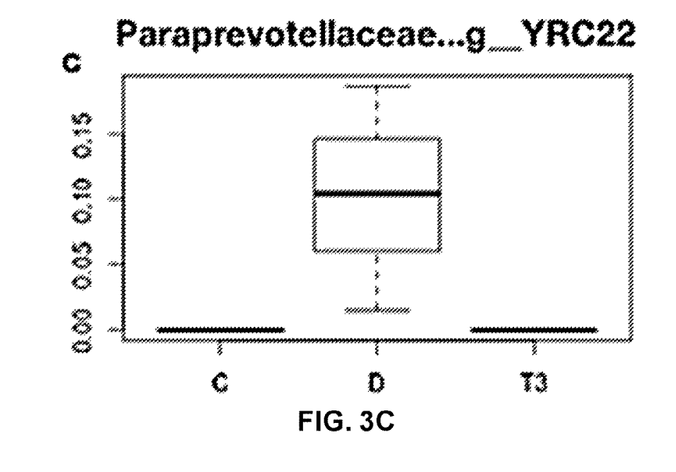
Figure 3D:
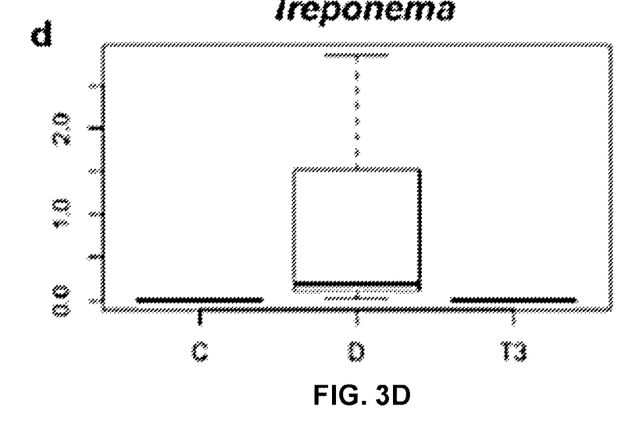

FIGS. 1A and 1B show alpha diversity analyses showing richness (number of different ASVs) and diversity (Shannon index), respectively, among samples from Healthy Control group (C), Diarrhea group (D) and Treatment group (T3). FIG. 2 shows a Bray-Curtis PCoA showing distinct gut bacterial communities among healthy Control group (C), Diarrhea group (D) and Treatment group (T3).

While no real statistical differences were found in terms of bacterial community richness (number of different ASVs, FIG. 1A) or diversity (Shannon index, FIG. 1B) between control (C), diarrhea (D) or treatment samples (P>0.05) there were numerical trends observed between the groups. Shannon's index accounts for both abundance and evenness of the species present. It was observed that pigs with diarrhea trended towards less microbiome diversity compared to healthy piglets. However, treatment of piglets that had diarrhea with ovotransferrin of the invention brought the microbiome diversity back to levels similar to the control piglets. This unexpected reversal of microbiome diversity with ovotransferrin actually was statistically significant when analyzing based on a Bray-Curtis distance PCoA. The microbiomes of samples within each group could be significantly discriminated based on a Bray-Curtis distance PCoA (PERMANOVA: P<0.001, R2-0.35) (FIG. 2).

FIGS. 3A, 3B, 3C, and 3D show microbiome species differences when diarrhea (D) occurs in piglets and when treated (T3) as compared to controls (C). Various indicator species analysis showed the ASVs or bacterial species/strains showed increases among diarrhea groups over the control group. The diarrhea samples were characterized by increased abundance of unclassified *Veilloneaceae, Entreobacteriaceae, Paraprevotellaceae*, and *Treponema* (Indicator value<0.98, P<0.05, FIGS. 3A-3D). Reductions to the initial control baselines of these species occurred when treatment with ovotransferrin was used in the piglets.

Results: This data shows that when piglets get diarrhea, the microbiome changes from a normally diverse population to a more restricted population. When pathogens take over and create enteric disease situations, the pathogen presence increases and there is less diversity in the microbiome. These findings suggest that ingredients of the invention such as ovotransferrin unexpectantly and surprisingly assist the restoration of the gut microbiome in weaned piglets with diarrhea by returning the normal diversity, presumably through elimination of species such as *Veilloneaceae, Entreobacteriaceae, Paraprevotellaceae* and *Treponema*. This allows for restoration of the microbiome in the gut of animals and resumption of a healthy productive life for the animal.

Example 7

Powdered components of the invention were mixed together to create a ratio of 40:40:20 of ovotransferrin to chitosan to *Curcumin*. The invention was then used to treat a dairy herd that had an enteric health problem despite antibiotic treatments with an overall newborn calf loss rate of 35%. This rate was due to outright calf death (19%) or culling of sick calves as a result of enteric infections (16%). The enteric disease diagnosed was *Salmonella* Dublin. The mixture of the invention was then given to 107 newborn calves at a rate of 7 grams per calf per day for 28 days in a row directly by bottle or combined with food. No other treatments were given. At the end of the 28-day treatment 100% of the treated animals had survived and all 107 treated calves were kept within the herd to lead a productive life. Reducing a 35% cull rate to a 0% cull rate resulted in a significant cost savings to the farm and hence profitability. These results show the surprising efficacy of the invention for maintaining and improving health in animals affected by various enteric diseases.

BIBLIOGRAPHY

Arabkhazaeli F., Modrisanei M, Nabian S., Mansoori B. and Madani A. Evaluating the Resistance of *Eimeria* Spp. Field Isolates to Anticoccidial Drugs Using Three Different Indices. Iran J Parasitol. 2013 April-June; 8(2): 234-241.

Epstein, J.; Sanderson, I. R.; MacDonald, T. T. *Curcumin* as a therapeutic agent: the evidence from in vitro, animal and human studies. British Journal of Nutrition, 2010, 103, 11, pp 1545-1557.

FDA 2017; https://www.fda.gov/animalveterinary/developmentapprovalprocess/ucm449019.htm Giansanti F., Loris Leboffe, Francesco Angelucci and Giovanni Antonini. The Nutraceutical Properties of Ovotransferrin and Its Potential Utilization as a Functional Food. Nutrients 2015, 7, 9105-9115.

Kantere, M., Athanasiou L. V., Chatzopoulos D. C., Spyrou V., Valiakos G., Kontos V. and Billinis C. Enteric Pathogens of Dogs and Cats with Public Health Implications. American Journal of Animal and Veterinary Sciences 9 (2): 84-94, 2014

Lam G, Apostolopoulos V, Zulli A, Nurgali K. NADPH oxidases and inflammatory bowel disease. Curr Med Chem. 2015; 22 (17) 2100-9.

Petri W A, Miller M, Binder H J, Levine M M, Dillingham R, and Guerrant R L. Enteric infections, diarrhea, and their impact on function and development. The Journal of Clinical Investigation, 2008; 118 (4) 1277-1290.

Pircalabioru et al. Defensive mutualism rescues NADPH oxidase inactivation in gut infection. Cell Host & Microbe 19, 651-663 May 11, 2016.

Ragab M. EL-Sabagh, Mabrouk, Attia Abd Eldaim. Effects of *Spirulina Platensis* Algae on Growth Performance, Antioxidative Status and Blood Metabolites in Fattening Lambs. Journal of Agricultural Science, Vol 6, No 3 p 92-98. 2014.

Raafat D., Kristine von Bargen, Albert Haas, and Hans-Georg Sahlahboub & Mohamed Abdel-Daim. Insights into the Mode of Action of Chitosan as an Antibacterial Compound. Applied and Environmental Microbiology, June 2008, p. 3764-3773 Vol. 74.

Talukder M J R and Harada E. Bovine lactoferrin protects lipopolysaccharide-induced diarrhea modulating nitric oxide and prostaglandin E2 in mice. Can. J. Physiol. Pharmacol. 2007, 85(2): 200-8.

Talukder J R, Ashley Griffin, Antara Jaima, Brittney Boyd, and Jaleesa Wright, Can. J. Lactoferrin ameliorates prostaglandin E2-mediated inhibition of Na-glucose cotransport in enterocytes. Physiol. Pharmacol. 92: 9-20 (2014).

What is claimed is:

1. A method of treating an animal that has an enteric disease, the method comprising orally administering to the animal in need thereof a composition comprising therapeutically effective amounts of a powdered iron-binding glycoprotein and a powdered chitosan polysaccharide, to effectively treat the enteric disease in the animal, wherein, when administered, the powdered chitosan polysaccharide is present in the composition in a form of chitosan polysaccharide particles consisting of chitosan polysaccharide.

2. The method of claim 1, wherein the administering is effective to reduce a symptom of the enteric disease in the animal.

3. The method of claim 1, wherein the administering is effective to increase weight gain in the animal.

4. The method of claim 1, wherein the administering is effective to increase gut microbiome diversity in the animal.

5. The method of claim 1, wherein the administering is effective to prolong survival of the animal.

6. The method of claim 1, wherein the enteric disease is a pathogenic microbial infection.

7. The method of claim 1, wherein the animal exhibits diarrhea.

8. The method of claim 7, wherein the administering is effective to reduce the diarrhea in the animal, increase weight gain in the animal, increase gut microbiome diversity in the animal, prolong survival of the animal, or any combination thereof.

9. The method of claim 7, wherein the administering is effective to reduce the diarrhea in the animal.

10. The method of claim 1, wherein the iron-binding glycoprotein is selected from the group consisting of ovotransferrin, transferrin, lactoferrin, and ferritin.

11. The method of claim 1, wherein the iron-binding glycoprotein is ovotransferrin.

12. The method of claim 1, wherein the composition further comprises *Curcumin*.

13. The method of claim 1, wherein the iron-binding glycoprotein is ovotransferrin and the composition further comprises *Curcumin*.

14. The method of claim 1, wherein the composition further comprises at least one electrolyte selected from the group consisting of sodium chloride, sodium citrate, potassium chloride, glucose, sucrose, and sodium bicarbonate.

15. A method of treating an animal that has an enteric disease, the method comprising orally administering to the animal in need thereof a composition comprising therapeutically effective amounts of an iron-binding glycoprotein and a chitosan polysaccharide, to effectively treat the enteric disease in the animal, wherein, prior to the administering, the iron-binding glycoprotein and the chitosan polysaccharide are present in a powder composition as powdered iron-binding glycoprotein and powdered chitosan polysaccharide, and wherein the powder composition is:
- administered in dry form to the animal;
- mixed directly with an animal feed and administered in combination with the animal feed to the animal;
- mixed with a liquid and administered in combination with the liquid to the animal; or
- mixed with a liquid that is sprayed on, added to, or mixed with an animal feed and administered in combination with the animal feed to the animal.

16. The method of claim 15, wherein the powder composition is administered in dry form to the animal.

17. The method of claim 15, wherein the powder composition is mixed directly with an animal feed and administered in combination with the animal feed to the animal.

18. The method of claim 15, wherein the powder composition is mixed with a liquid and administered in combination with the liquid to the animal.

19. The method of claim 15, wherein the powder composition is mixed with a liquid that is sprayed on, added to, or mixed with an animal feed and administered in combination with the animal feed to the animal.

\* \* \* \* \*